United States Patent
Jacob

(10) Patent No.: US 11,932,907 B2
(45) Date of Patent: Mar. 19, 2024

(54) FETAL SEX DETERMINATION USING CAPILLARY BLOOD FROM UPPER ARM

(71) Applicant: GATEWAY GENOMICS, LLC, La Jolla, CA (US)

(72) Inventor: Christopher Jacob, La Jolla, CA (US)

(73) Assignee: Gateway Genomics, LLC, La Jolla, CA (US)

( * ) Notice: Subject to any disclaimer, the term of this patent is extended or adjusted under 35 U.S.C. 154(b) by 0 days.

(21) Appl. No.: 18/307,666

(22) Filed: Apr. 26, 2023

(65) Prior Publication Data

US 2023/0257811 A1 Aug. 17, 2023

Related U.S. Application Data

(63) Continuation of application No. 17/762,680, filed as application No. PCT/US2020/052187 on Sep. 23, 2020, now abandoned.

(60) Provisional application No. 62/936,329, filed on Nov. 15, 2019, provisional application No. 62/903,945, filed on Sep. 23, 2019.

(51) Int. Cl.
*C12P 19/34* (2006.01)
*C12Q 1/6806* (2018.01)
*C12Q 1/6879* (2018.01)

(52) U.S. Cl.
CPC .......... *C12Q 1/6879* (2013.01); *C12Q 1/6806* (2013.01)

(58) Field of Classification Search
CPC .............................. C12Q 1/686; C12Q 1/6879
See application file for complete search history.

(56) References Cited

U.S. PATENT DOCUMENTS

| | | | |
|---|---|---|---|
| 10,335,078 B2 | 7/2019 | Kvam et al. | |
| 2017/0067803 A1 | 3/2017 | Jackson et al. | |
| 2019/0144919 A1 | 5/2019 | Jackson et al. | |
| 2019/0216380 A1 | 7/2019 | Ivosevic et al. | |
| 2019/0369113 A1* | 12/2019 | Shuford | G01N 30/7233 |
| 2020/0163603 A1 | 5/2020 | Jordan et al. | |

FOREIGN PATENT DOCUMENTS

WO WO 2016/161083 A1 10/2016

OTHER PUBLICATIONS

Catala et al., Metabolomics 14(100), 1-9 (2018). (Year: 2018).*
International Search Report and Written Opinion dated Jan. 6, 2021 for International Patent Application No. PCT/US2020/052187.
Primacio, R et al.. "Early Fetal Sex Determination using Cell-Free DNA in Micro-Volume of 1-4 Maternal Plasma", Journal of Pregnancy and Child Health, Dec. 2017.
Your DNA. "SneakPeek Early Gender DNA Test", downloaded from https://yourdna.com/sneak-peek-gender-test. Aug. 21, 2019.
Primacio et al., Abstract 2046F: "Maternal capillary blood: A new source of circulating cell-free fetal DNA for noninvasive prenatal testing"; published in Poster Abstracts of American Society of Human Genetics 65th Annual Meeting, 2015 at p. 701.
Milot and Jacob, Abstract P-70: "Finger stick self-collection of maternal blood for noninvasive prenatal testing"; published in Prenatal Diagnosis2017, 37 (Suppl. 1) at pp. 52-53.
Breitbach et al., "Direct measurement of cell-free DNA from serially collected capillary plasma during incremental exercise"; J Appl Physiol117: 119-130, 2014.
Gateway Genomics Press Release, "Gateway Genomics Previews Advanced Technology for the Future of Genetic Testing at the International Society for Prenatal Diagnosis"; Businesswire (Aug. 4, 2015).
Third Party Submission Under 37 C.F.R. § 1.290 filed on Jul. 12, 2022 in U.S. Appl. No. 17/547,920.
Hoang, et al., "SnakePeek Snap: A Painless Microneedle-Based Push-Button Device for Early Fetal Sex Determination", International Journal of Pregnancy & Child Birth, vol. 7, Issue 3, 2021.

* cited by examiner

*Primary Examiner* — Kenneth R Horlick
(74) *Attorney, Agent, or Firm* — Knobbe, Martens, Olson & Bear, LLP

(57) ABSTRACT

The disclosure relates to methods, compositions, and kits for the early determination of the sex of a fetus. The disclosure also provides methods, compositions, and kits for detecting fetal nucleic acids in biological samples (e.g., cell-free fetal DNA). An embodiment includes a method of improving the accuracy of fetal sex determination by reducing a level of contaminating DNA in a blood sample from a pregnant human subject, comprising obtaining a capillary blood sample collected from the upper arm using a push-button blood collection device, thereby reducing a level of contaminating DNA from a non-maternal and non-fetal source in the capillary blood sample as compared to a blood sample collected from a site on the finger or hand of the subject, and detecting the presence or absence of fetal Y-chromosome to determine the sex of the fetus.

14 Claims, No Drawings

FETAL SEX DETERMINATION USING CAPILLARY BLOOD FROM UPPER ARM

CROSS-REFERENCE TO RELATED APPLICATIONS

This application is a continuation of U.S. patent application Ser. No. 17/762,680, filed Mar. 22, 2022, which is a U.S. National Phase under 35 U.S.C. § 371 of International Patent Application No. PCT/US2020/052187, filed Sep. 23, 2020, which claims the benefit of priority of U.S. Provisional Patent Applications No. 62/903,945, filed Sep. 23, 2019, and No. 62/936,329, filed Nov. 15, 2019, each of which is hereby expressly incorporated by reference in its entirety.

FIELD OF THE INVENTION

The disclosure relates to methods, compositions, and kits for the early determination of the sex of a fetus. The disclosure also provides methods, compositions, and kits for detecting fetal nucleic acids in biological samples (e.g., cell-free fetal DNA).

BACKGROUND OF THE INVENTION

There are approximately 4 million live births in the United States each year. More than two-thirds of expectant parents want to know the sex of their baby as early as practical into pregnancy. There are currently a limited number of options for learning the sex of a fetus available to expectant parents during the 40 weeks of the typical human gestational period.

Ultrasound imaging has been used safely for decades and is considered highly accurate for determining fetal sex at 18 to 20 weeks of gestation. Amniocentesis may be used for determining fetal sex with high accuracy between 15 to 18 weeks gestational age but carries a miscarriage risk and is not available to most women. More recently, non-invasive prenatal testing (NIPT) has been made available for high risk pregnancies and is highly accurate for determining fetal sex from maternal blood between 11- and 13-weeks gestational age, and on average 15 weeks (G. Allahbadia, (2015) J Obstet Gynaecol India. 65(3):141-145). All methods of NIPT require a minimum fetal fraction for accurate trisomy screening, commonly estimated at 4% (G. Ashoor et al. (2013) Ultrasound in Obstetrics & Gynecology 41:26-32). Since fetal fraction is generally less than 4% at earlier time points in pregnancy, NIPT is not generally used for prenatal testing prior to 11 weeks.

Fetal sex is determined at the time of conception, approximately 2 weeks gestational age. There is a need in the art for methods and kits useful for determining fetal sex between 2- and 11-weeks gestational age. Additionally, there is a need in the art for compositions for detecting fetal nucleic acids in biological samples. The present disclosure meets some or all of these needs by providing highly accurate, noninvasive methods for determining fetal sex at earlier timepoints than any conventional method. The present disclosure further provides novel methods, assays, kits, and compositions for detecting fetal nucleic acids and determining fetal sex in early pregnancy (e.g., 4 to 8 weeks gestational age).

SUMMARY OF THE INVENTION

The present disclosure provides methods of determining the sex of a fetus in a pregnant subject, typically a human subject, comprising: obtaining a biological sample from the subject; and detecting fetal Y-chromosome nucleic acids in the sample, thereby determining the sex of the fetus. In some embodiments, the methods of the disclosure further comprise enriching the sample for fetal nucleic acids. In some aspects, the enrichment is achieved by separating plasma from whole blood, by selectively capturing fetal nucleic acids from the biological sample, or by selectively degrading maternal nucleic acids in the biological sample. In some embodiments, the Y-chromosome nucleic acids are cell-free fetal nucleic acids (e.g., cffDNA). In some embodiments, the Y-chromosome nucleic acids are genomic fetal nucleic acids from a fetal cell (e.g., gfDNA).

The disclosure provides methods for isolating and concentrating fetal nucleic acids in biological samples from pregnant subjects, (e.g. human subjects). In some embodiments, the methods further comprise isolating fetal nucleic acids with a silica column or magnetic beads. In other embodiments, the methods further comprise concentrating the fetal nucleic acids in the biological sample using heat. In yet other embodiments, the methods further comprise isolating fetal nucleic acids by incubating the sample with an enzyme (e.g., proteinase K).

The methods, compositions, and kits of the disclosure provide optimal sensitivity, specificity, and accuracy for fetal sex determination. In some embodiments, the methods of the disclosure determine the sex of the fetus with at least 40%, 50%, 60%, 70%, 75%, 80%, 85%, 90%, 95%, 99%, or 100% specificity. In some aspects, the methods of the disclosure determine the sex of the fetus with at least 40%, 50%, 60%, 70%, 75%, 80%, 85%, 90%, 95%, 99%, or 100% sensitivity. In yet other aspects, the methods of the disclosure determine the sex of the fetus with at least 40%, 50%, 60%, 70%, 75%, 80%, 85%, 90%, 91%, 92%, 93%, 94%, 95%, 96%, 97%, 98%, 99%, or 100% accuracy.

In some embodiments, the false positive rate of the methods and kits of the disclosure is less than 1%, less than 2%, less than 3%, less than 4%, less than 5%, less than 6%, less than 7%, less than 8%, less than 9%, less than 10%, less than 20%, or less than 25%.

The performance of the methods, compositions, and kits of the disclosure have been determined in multiple populations. In some embodiments, the performance of the methods, compositions, and kits of the disclosure have been determined in a population of at least 10, 20, 30, 40, 50, 60, 70, 80, 90, 100, 150, 200, 300, 400, 500, and/or 1,000 or more pregnant subjects.

The methods, compositions, and kits of the disclosure may be used at various gestations ages of pregnancy. In some embodiments, the gestational age of the fetus is 2 weeks, 3 weeks, 4 weeks, 5 weeks, 6 weeks, 7 weeks, 8 weeks, 9 weeks, 10 weeks, 11 weeks, or 12 weeks. In some embodiments, the gestational age of the fetus is 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days 42 days, 49 days, 56 days, 63 days, 70 days, 77 days, or 84 days.

The disclosure provides methods, compositions, and kits for detecting Y-chromosome nucleic acids in a biological sample from a pregnant subject. In some embodiments, the detecting comprises performing microarray analysis, polymerase chain reaction (PCR), or sequencing. In some embodiments, the PCR is quantitative PCR (qPCR) or digital PCR. In other embodiments the qPCR is a TaqMan assay. In other embodiments, the PCR is a nested PCR, a duplex PCR, or a multiplex PCR. In other embodiments, the reaction volume of the PCR is 2 ul, 3 ul, 4 ul, 5 ul, 10 ul, 15 ul, 20 ul, 25 ul, or 50 ul. In yet other embodiments, the mastermix used in the PCR contains Uracil N Glycosylase (UNG).

In other embodiments, the methods further comprise interpreting data generated when detecting the Y-chromosome DNA. In some embodiments, the interpreting is performed using a machine learning algorithm, a cycle-threshold (CT) algorithm, or artificial intelligence.

In some embodiments, the biological sample is incubated with a preservative. In some embodiments, the preservative is an anti-coagulant (e.g., ethylenediaminetetraacetic acid (EDTA), ethylene glycol-bis((3-aminoethyl ether)-N,N,N', N'-tetraacetic acid (EGTA), heparin), an antimicrobial (e.g., imidazolidinyl urea), a sugar, and/or an amino acid. In other embodiments, the preservative is a solid, a liquid, and/or a gel.

Various types of biological samples can be used with the methods, compositions, and kits of the disclosure. In some embodiments, the sample is blood, plasma, serum, saliva, urine, and/or cervical mucus. In other embodiments, the sample is maternal blood, maternal plasma, or maternal serum. In yet other embodiments, the volume of the sample obtained from the subject is 10 ul to 10 ml. In some embodiments, the volume of the sample used to detect Y-chromosome DNA is a microvolume. In certain embodiments, the microvolume is about 1,000 ul, about 900 ul, about 800 ul, about 700 ul, about 600 ul, about 500 ul, about 400 ul, about 300 ul, about 200 ul, about 150 ul, about 100 ul, about 50 ul, about 25 ul, about 10 ul. The biological sample can be processed at any time after being collected from the subject. In some embodiments, the biological sample is processed within 1 hour, within 24 hours, or within 48 hours. In other embodiments, the biological sample is not processed for at least 6 hours, at least 8 hours, at least 10 hours, at least 12 hours, at least 1 day, at least 2 days, at least 3 days, at least 1 week, at least, 2 weeks, or at least 4 weeks. In other embodiments, at least 12 hours, at least 18 hours, at least 24 hours, or at least 36 hours elapses between a time of blood collection and a time of any testing or screening of a collected blood sample, and or isolation of the cell-free nucleic acids. In yet other embodiments at least 24 hours elapses between a time of blood collection and a time of any testing or screening of a collected blood sample, and or isolation of the cell-free nucleic acids. In still other embodiments, more than 24 hours elapses between a time of blood collection and a time of any testing or screening of a collected blood sample, and or isolation of the cell-free nucleic acids.

The methods and kits of the disclosure may include instructions for decontaminating the site on the pregnant subject where the sample will be collected. In certain embodiments, the decontamination is performed by applying bleach to the site of collection, by applying an alcohol wipe to the site of collection, by treating the site of collection with ultra-violet light, by applying chlorhexidine gluconate, hydrogen peroxide, and/or iodine to the site of collection, by applying a brush (e.g., a nail brush) to the site of the collection.

The present disclosure further provides kits for obtaining a biological sample from a pregnant subject. The kits may comprise a blood collection tube, a lancet or a device useful for obtaining venous or capillary blood from the subject, a tourniquet, a bandage, an alcohol swab, a nail or skin brush, and instructions for using the kits. In some embodiments, the kits further comprise a decontaminating agent. In certain embodiments, the decontaminating agent is bleach, an alcohol wipe, chlorhexidine gluconate, hydrogen peroxide, and/or iodine. In other embodiments, the device for obtaining venous or capillary blood is a lancet (e.g., BD Microtainer contact-activated lancet), a syringe, and/or a push-button blood collection device (e.g., a TAP device or a TASSO-SST device). In some embodiments, the biological sample is collected into a tube, onto a card, and/or a swab.

The present disclosure provides methods for detecting Y-chromosome DNA in biological samples from pregnant subjects. In some embodiments, a set of nucleic acid primers and/or probe are used to amplify and/or detect the Y-chromosome DNA in the sample. Primers and probes used in the methods of the disclosure may target one or more targets or target regions on the Y-chromosome (e.g., a gene on the Y-chromosome). In some embodiments, the target on the Y-chromosome is SRY, DYS, or DAZ. In some embodiments, the methods use one or more targets on the Y-chromosome to detect Y-chromosome DNA in the sample. In other embodiments, the target is a DNA sequence that is present in one or more locations on the Y-chromosome.

Kits of the disclosure include instructions for collecting the sample at various gestational ages. In some embodiments, the instructions provide for sample collection at gestational age of 2 weeks, 3 weeks, 4 weeks, 5 weeks, 6 weeks, 7 weeks, 8 weeks, 9 weeks, 10 weeks, 11 weeks, or 12 weeks. In some embodiments, the gestational age of the fetus is 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days 42 days, 49 days, 56 days, 63 days, 70 days, 77 days, or 84 days.

The methods, compositions, and kits of the disclosure can be used to detect very small amounts of Y-chromosome DNA in a biological sample from a pregnant subject. In some embodiments, the methods of the disclosure can detect about 1 to 0.1 genomic equivalent of cffDNA in a sample, about 0.9 genomic equivalent of cffDNA in a sample, about 0.8 genomic equivalent of cffDNA in a sample, about 0.7 genomic equivalent of cffDNA in a sample, about 0.6 genomic equivalent of cffDNA in a sample, about 0.5 genomic equivalent of cffDNA in a sample, about 0.4 genomic equivalent of cffDNA in a sample, about 0.3 genomic equivalent of cffDNA in a sample, about 0.2 genomic equivalent of cffDNA in a sample, about 0.1 genomic equivalent of cffDNA in a sample. In some embodiments, the fetal fraction in the biological sample is about 4%, about 3%, about 2%, about 1% or less than 1%.

In some embodiments, the disclosure provides a method comprising: a) obtaining or having obtained a maternal capillary blood sample comprising cell-free nucleic acids, wherein the volume of blood is 500 microliters or less, b) incubating the blood sample with a cell-free nucleic acid preservative, c) storing the blood sample in a tube for at least 1 day at ambient temperature prior to testing the blood sample, d) collecting 50 to about 250 microliters of plasma from the blood sample, e) isolating cell-free nucleic acids from the blood sample, f) detecting Y-chromosome DNA in the cell-free nucleic acids by performing quantitative PCR with all or a portion of the isolated cell-free nucleic acids, g) determining the sex of a fetus as male based on the detection of Y-chromosome DNA in the cell-free nucleic acids, wherein the gestational age of the fetus is 6 weeks to 8 weeks, wherein the accuracy of determining fetal sex is at least 99%.

In some embodiments, the disclosure provides a method comprising: a) obtaining or having obtained a maternal venous blood sample comprising cell-free nucleic acids, wherein the volume of blood is 10 milliliters or less, b) incubating the blood sample with a cell-free nucleic acid preservative, c) storing the blood sample in a tube for at least 1 day at ambient temperature prior to testing the blood sample, d) collecting about 50 microliters to about 5 milliliters of plasma from the blood sample, e) isolating cell-free nucleic acids from the blood sample, f) detecting Y-chromosome DNA in the cell-free nucleic acids by performing quantitative PCR with all or a portion of the isolated cell-free nucleic acids, g) determining the sex of a fetus is male based on the detection of Y-chromosome DNA in the cell-free nucleic acids, wherein the gestational age of the fetus is 6 weeks to 8 weeks, wherein the accuracy of determining fetal sex is at least 99%.

An aspect of the present disclosure is a method of determining the sex of a fetus in a pregnant subject, comprising: obtaining a biological sample from the subject; and detecting fetal Y-chromosome nucleic acids in the sample, thereby determining the sex of the fetus. In some embodiments, the method further comprises enriching the sample for fetal nucleic acids. In some embodiments the enrichment is achieved by separating plasma from whole blood, by selectively capturing fetal nucleic acids from the biological sample, and/or by selectively degrading maternal nucleic acids in the biological sample. In some embodiments the Y-chromosome nucleic acids are cell-free fetal nucleic acids or genomic fetal nucleic acids from a fetal cell. In some embodiments the method further comprises isolating and concentrating the fetal nucleic acids. In some embodiments the isolating is achieved with a silica column or magnetic beads. In some embodiments the sex of the fetus is determined with at least 90%, 95%, 96%, 97%, 98%, 99%, 99.1%, 99.2%, 99.3%, 99.4%, 99.5%, 99.6%, 99.7%, 99.8%, 99.9%, or 100% accuracy. In some embodiments the performance of the method has been determined in a population of at least 50 or more pregnant subjects. In some embodiments the gestational age of the fetus is selected from the group consisting of between 4 weeks and 8 weeks, not more than 56, 53, 49, 46, 42, 39, 35, 32, or 28 days or a range defined by any two of the preceding values, 35-53 days, 42-49 days and 42-53 days. In some embodiments the detecting comprises performing microarray analysis, polymerase chain reaction (PCR), or sequencing. In some embodiments the PCR is a real-time quantitative PCR. In some embodiments sample is blood, plasma, serum, saliva, urine, and/or cervical mucus. In some embodiments sample volume is selected from the volume of less than 1 ml, 750 µl, 500 µl, 250 µl, 200 µl, 175 µl, 150 µl, 125 µl, 100 µl, 75 µl, 50 µl, and 25 µl, and a range of 25-500 µl, 25-250 µl, 50-125 µl, and 100-250 µl. In some embodiments the biological sample is processed within 1 hour, within 24 hours, or within 48 hours. In some embodiments biological sample is incubated or mixed with a preservative. In some embodiments the biological sample is stored at ambient temperature for at least 12, 18, 24, 36 or 48 hours, 12-48 hours, 18-48 hours, 18-36 hours, or 18-24 hours, before processing, and wherein the biological sample is whole blood. In some embodiments the whole blood is capillary blood. In some embodiments method comprises: a) obtaining or having obtained a blood sample from a pregnant subject, wherein the volume of blood is 80-10,000 µl, 80-5,000 µl, or 80-1,000 µl of venous blood, or 80-500 µl, or 80-250 µl of capillary blood; b) mixing the blood sample with a cell-free nucleic acid preservative; c) storing the blood sample for at least 12, 18, 24, 36 or 48 hours, 18-48 hours, 18-36 hours, or 18-24 hours, at ambient temperature; d) collecting 40-5,000 µl, 40-2,500 µl, or 40-500 µl of plasma from the venous blood sample, or 40-250 µl or 40-125 µl of plasma from the capillary blood sample; e) isolating cell-free nucleic acids from the plasma; f) detecting Y-chromosome DNA in the cell-free nucleic acids by performing quantitative PCR with all or a portion of the isolated cell-free nucleic acids, wherein the gestational age of the fetus is not more than 56, 53, 49, 46, 42, 39, 35, 32, or 28 days, or 35-53 days, 42-49 days or 42-53 days, and wherein the accuracy of determining fetal sex is at least 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% determined in a population of at least 50 or more pregnant subjects. In some embodiments the method further comprises g) determining the sex of a fetus as male based on the detection of Y-chromosome DNA in the cell-free nucleic acids, or female based on the absence of detection of Y-chromosome DNA in the cell-free nucleic acids. In some embodiments the volume of blood is 80-500 µl of capillary blood, wherein 40-250 µl of plasma is collected, wherein the gestational age of the fetus is 42-53 days and the accuracy of the test is at least 99%. In some embodiments the sample is incubated or mixed with a cell-free nucleic acid preservative, wherein the preservative is an anti-coagulant (e.g., ethylenediaminetetraacetic acid (EDTA), ethylene glycol-bis((3-aminoethyl ether)-N,N,N', N'-tetraacetic acid (EGTA), heparin), an antimicrobial, a sugar, and/or an amino acid. In some embodiments the sample is a capillary blood sample collected from the upper arm of the subject. In some embodiments the method comprises decontaminating the sample collection site. In some embodiments the sample collection site is not a hand or finger. In some embodiments the method does not comprises decontaminating the sample collection site. In some embodiments the subject is human.

An aspect of the disclosure is a kit for collecting a biological sample from a pregnant subject for determining fetal sex, the kit comprising a blood collection tube, a lancet or a device for obtaining venous or capillary blood from the subject, a tourniquet, a bandage, an alcohol swab, optionally a nail or skin brush, and instructions. In some embodiments the kit further comprises a decontaminating agent. In some embodiments the decontaminating agent is bleach, an alcohol wipe, chlorhexidine gluconate, hydrogen peroxide, and/ or iodine. In some embodiments the instructions provide for sample collection at gestational age of 2 weeks, 3 weeks, 4 weeks, 5 weeks, 6 weeks, 7 weeks, 8 weeks, 9 weeks, 10 weeks, 11 weeks, or 12 weeks. In some embodiments the subject is human These and other embodiments of the present disclosure will readily occur to those of skill in the art in light of the disclosure herein, and all such embodiments are specifically contemplated.

Each of the limitations of the disclosure can encompass various embodiments of the disclosure. It is, therefore, anticipated that each of the limitations of the disclosure involving any one element or combinations of elements can be included in each aspect of the disclosure. This disclosure is not limited in its application to the details of construction and the arrangement of components set forth in the following description. The disclosure is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items. It must be noted that as used herein and in the appended claims, the singular forms "a," "an," and "the" include plural references unless context clearly dictates otherwise.

DESCRIPTION OF THE INVENTION

It is to be understood that the disclosure is not limited to the particular methodologies, protocols, cell lines, assays, and reagents described herein, as these may vary. It is also to be understood that the terminology used herein is intended to describe particular embodiments of the present disclosure, and is in no way intended to limit the scope of the present disclosure as set forth in the appended claims.

It must be noted that as used herein and in the appended claims, the singular forms "a," "an," and "the" include plural references unless context clearly dictates otherwise. Thus, for example, a reference to "a nucleic acid" includes a plurality of such nucleic acids, a reference to a "composition" is a reference to one or more compositions and to equivalents thereof known to those skilled in the art, and so forth.

Unless defined otherwise, all technical and scientific terms used herein have the same meanings as commonly understood by one of ordinary skill in the art to which this disclosure belongs when read in light of the present disclosure. Although any methods and materials similar or equivalent to those described herein can be used in the practice or testing of the present disclosure, the preferred methods, devices, and materials are now described. All publications cited herein are incorporated herein by reference in their entirety for the purpose of describing and disclosing the methodologies, reagents, and tools reported in the publications that might be used in connection with the disclosure. Nothing herein is to be construed as an admission that the disclosure is not entitled to antedate such disclosure by virtue of prior invention.

The practice of the present disclosure will employ, unless otherwise indicated, conventional methods of chemistry, biochemistry, molecular biology, cell biology, genetics, immunology and pharmacology, within the skill of the art. Such techniques are explained fully in the literature. See, e.g., Gennaro, A. R., ed. (1990) Remington's Pharmaceutical Sciences, 18th ed., Mack Publishing Co.; Colowick, S. et al., eds., Methods In Enzymology, Academic Press, Inc.; Handbook of Experimental Immunology, Vols. I-IV (D. M. Weir and C. C. Blackwell, eds., 1986, Blackwell Scientific Publications); Maniatis, T. et al., eds. (1989) Molecular Cloning: A Laboratory Manual, 2nd edition, Vols. I-III, Cold Spring Harbor Laboratory Press; Ausubel, F. M. et al., eds. (1999) Short Protocols in Molecular Biology, 4th edition, John Wiley & Sons; Ream et al., eds. (1998) Molecular Biology Techniques: An Intensive Laboratory Course, Academic Press); PCR (Introduction to Biotechniques Series), 2nd ed. (Newton & Graham eds., 1997, Springer Verlag).

The disclosure relates, in part, to the discovery that the sex of a fetus can be determined with high accuracy at very early gestational ages by detecting Y-chromosome DNA in a biological sample obtained from a pregnant subject, e.g., 4 weeks to 8 weeks gestational age. In some embodiments, the sex of a fetus can be determined with high accuracy, for example, at least 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9%, at very early gestational ages, for example not more than 56, 53, 49, 46, 42, 39, 35, 32, or 28 days gestational age, or a range defined by any two of the preceding values, for example 35-53 days, 42-53 days, or 42-49 days.

The disclosure is based, in part, on the discovery of unexpected improvements in sensitivity, specificity, and accuracy of methods, compositions, and kits of the disclosure for determining the sex of a fetus in biological samples from a pregnant subject, e.g., greater than 99% accuracy at determining fetal sex in a blood sample obtained from a pregnant subject at 6 weeks gestation, or earlier. The disclosure demonstrates that fetal nucleic acids present in the maternal circulation may be detected at very early time points in pregnancy to determine fetal sex in a subject.

The disclosure provides methods for determining fetal sex in a pregnant subject. In some embodiments, the methods determine fetal sex in the subject with at least 99% accuracy. In some embodiments, the methods determine fetal sex in the subject with at least 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% accuracy, including 100% accuracy, or a range defined by any two of the preceding values, for example 98%-100%, 99.0%-100%.

The disclosure also provides compositions for use in the methods described herein. Such compositions may include one or more of compounds, primers, probes, preservatives, including anticoagulants, cell fixatives, protease inhibitors, phosphatase inhibitors, proteins, DNA or RNA preservatives.

The present disclosure further provides kits for collecting biological samples from pregnant subjects or for determining fetal sex in a subject. In these embodiments, the kits comprise one or more of a blood collection tube, a lancet or a device useful for obtaining venous or capillary blood from the subject, a tourniquet, a bandage, an alcohol swab, a nail or skin brush, and instructions for using the kits.

The section headings are used herein for organizational purposes only, and are not to be construed as in any way limiting the subject matter described herein.

Biological Sample

The disclosure provides methods, compositions, and kits for determining the sex of a fetus in a pregnant subject. Generally, the methods of the disclosure involve the detection of Y-chromosome DNA in a biological sample obtained from a pregnant subject. A biological sample comprising fetal nucleic acids may be obtained from a pregnant subject. The biological sample obtained from the subject is typically blood, but can be any sample from bodily fluids, tissue or cells comprising the nucleic acids to be analyzed. The biological sample may include, but is not limited to, whole blood, serum, plasma, urine, a cervical swab, saliva, a buccal swab, and/or amniotic fluid.

In some embodiments, the biological sample of the disclosure can be obtained from blood. In some embodiments, about 0.1-10 mL of blood is obtained from a subject. In other embodiments, about 10-50 mL of blood is obtained from a subject. In some embodiments, the amount of blood obtained from the subject is, is about, is at least, is at least about, is not more than, or is not more than about, 40, 50, 60, 70, 80, 90, 100, 250, 500, 750, or 1000 µl, or 1, 5, or 10 ml, or a range defined by any two of the preceding values, for example, 1-500 µl, 50-1000 µl, 50 µl-5 ml, and 100 µl-10 ml. Blood can be obtained from any suitable area of the body, including an arm, a leg, a finger, or blood accessible through a central venous catheter. In some embodiments, blood is collected from the finger using a lancet. In other embodiments, blood is collected from the arm via venipuncture. In yet other embodiments, blood is collected from the arm using a TAP device (Seventh Sense Biosystems, MA) or a TASSO-SST device (Tasso Inc., WA). In some embodiments, the site of blood collection is a site less likely to be contaminated with foreign DNA. In some embodiments the site of blood collection is on the torso (e.g. stomach, side, back, shoulder), hip, upper leg (e.g. thigh), lower leg (e.g. calf). In other embodiments, the site of blood collection is the upper arm (i.e., located between the shoulder joint and elbow joint). In some embodiments, the site of blood collection is not the finger, or not the hand. In some embodiments the blood is not venous blood. In some embodiments, blood is collected following a treatment or activity. For example, blood can be collected following a medical exam. The timing of collection can also be coordinated to increase the amount of fetal nucleic acids present in the sample. For example, blood can be collected following exercise.

Blood may be combined with various components following collection to preserve or prepare samples for subsequent techniques. For example, in some embodiments, blood is treated with an anticoagulant, a cell fixative, a protease inhibitor, a phosphatase inhibitor, a protein, a DNA, or an RNA preservative following collection. In some embodiments, the biological sample is incubated with a preservative. In some embodiments, the preservative is an anticoagulant (e.g., ethylenediaminetetraacetic acid (EDTA), ethylene glycol-bis((3-aminoethyl ether)-N,N,N',N'-tetraacetic acid (EGTA), heparin), an antimicrobial (e.g., imidazolidinyl urea), a sugar, and/or an amino acid. In other embodiments, the preservative is a solid, a liquid, and/or a gel. In some embodiments, blood is collected via venipuncture using vacuum collection tubes containing an anticoagulant such as EDTA, EGTA, or heparin. Blood can also be collected using a heparin-coated syringe and hypodermic needle. Blood can also be combined with components that will be useful for subsequent analysis of the fetal nucleic acids contained therein.

The volume of the biological sample obtained from the subject may be 10 ul to 10 ml. In some embodiments, the volume of the sample used to detect Y-chromosome DNA is a microvolume. In certain embodiments, the microvolume is about 1,000 ul, about 900 ul, about 800 ul, about 700 ul, about 600 ul, about 500 ul, about 400 ul, about 300 ul, about 200 ul, about 150 ul, about 100 ul, about 50 ul, about 25 ul, about 10 ul. Blood samples are typically processed within a few hours from the time of collection to prevent significant degradation of the nucleic acids by enzymes present in blood. The methods of the disclosure enable the biological sample to be processed up to several months after being collected from the subject. In some embodiments, the biological sample is processed within 1 hour, within 24 hours, or within 48 hours. In other embodiments, the biological sample is not processed for at least 6 hours, at least 8 hours, at least 10 hours, at least 12 hours, at least 1 day, at least 2 days, at least 3 days, at least 1 week, at least, 2 weeks, or at least 4 weeks.

The biological sample should be free of contaminating DNA from a non-maternal or non-fetal source (e.g., touch DNA from another person). In various methods of the disclosure, the presence or absence of Y-chromosome DNA in the biological sample is used to determine if a fetus is male or female. Contaminating Y-chromosome DNA (i.e., non-fetal Y-chromosome DNA) has the potential to produce a false positive result for a fetal sex assay of the disclosure. In some aspects, maternal blood is collected from a site on the body which is generally free of contaminating Y-chromosome DNA. In some embodiments, the site of blood collection is the upper arm. In some embodiments, the site of blood collection is on the torso (e.g. stomach, side, back, shoulder), hip, upper leg (e.g. thigh), upper arm, lower leg (e.g. calf). In some embodiments, the site of blood collection is not the finger, or not the hand. In some embodiments, a TAP blood specimen collection device is used to collect a maternal blood sample. The TAP Blood Collection Device is a single-use, sterilized blood collection and transportation device that uses a combination of two mechanisms, capillary action and vacuum extraction. The device consists of an integrated reservoir with a visual fill indicator window. The device is designed to collect and contain approximately 100-500 μL of capillary whole blood. The internal fluid path is coated with lithium heparin, EDTA, EGTA, or other anticoagulants and/or preservatives. The top of the device includes a green button or plunger and a fill indicator window. The base of the device includes a release liner that covers a layer of hydrogel adhesive. The hydrogel adhesive seals to the skin and holds the device in place during use. The TAP device contains an array of microneedles in order to puncture through the skin. The microneedles are activated by a spring, released by pushing a button or plunger on the device. The device is provided sterile in a tray or foil pouch. A preservative or cell stabilizer can optionally be used in the TAP device to allow for DNA analysis more than 6 hours after a blood sample is collected. In some embodiments, the blood sample is processed 6 hours, 8 hours, 10 hours, 12 hour, 24 hours, 48 hour, 72 hours, 96 hours, 120 hours, 144 hours, or 168 hours after collection. In some embodiments, the blood is stabilized in the TAP device with a preservative such that DNA concentration in the plasma portion of the blood sample remain relatively constant for up to 7 to 14 days post collection. In some embodiment, the preservative in the TAP device prevents significant genomic DNA contamination in blood samples for up to 7 to 14 days post collection. In other embodiments, the blood is stabilized in the TAP device with a preservative such that DNA concentration in the plasma portion of the blood sample remain relatively constant for up to 3 to 7 days post collection. In some embodiments, the site of blood collection is a site less likely to be contaminated with foreign DNA. In some embodiments the site of blood collection is on the torso (e.g. stomach, side, back, shoulder), hip, upper leg (e.g. thigh), lower leg (e.g. calf). In other embodiments, the site of blood collection is the upper arm (i.e., located between the shoulder joint and elbow joint). In some embodiments, the site of blood collection is not the finger, or not the hand. In some embodiments the blood is not venous blood.

In some embodiments, the TAP device or TASSO-SST device including a preservative, facilitates storage of the blood sample collected in the tube at room temperature for at least, or about 14 days without cell lysis and without cell-free nucleic acid degradation of the blood sample due to DNase and RNase activity after blood draw.

Pregnant Subjects

The disclosure provides methods, compositions, and kits for the early determination of the sex of a fetus in a pregnant subject. In some embodiments the subject is a human subject. The pregnancy may be the result of natural conception (i.e., a natural pregnancy) of result from use of assisted reproductive technology (e.g., in-vitro fertilization). In some embodiments, the pregnant subject has used assisted reproductive technology (ART) to become pregnant. In some aspects, the assisted reproductive technology is in-vitro fertilization, use of fertility medication (e.g., clomifene), ovulation induction, cryopreservation, and/or intracytoplasmic sperm injection. In some embodiments, the pregnant subject has a high-risk pregnancy. In other embodiments, the pregnant subject is a carrier of a sex-linked recessive disease or disorder.

The disclosure provides methods, compositions, and kits useful for determining fetal sex at various timepoints in pregnancy. Gestational age is a measure of the age of a pregnancy which is taken from the beginning of the woman's last menstrual period (LMP), or the corresponding age of the gestation as estimated by a more accurate method if available. Such methods include adding 14 days to a known duration since fertilization (as is possible in in vitro fertilization), or by obstetric ultrasonography. In some embodiments, the gestational age of the fetus is 2 weeks, 3 weeks, 4 weeks, 5 weeks, 6 weeks, 7 weeks, 8 weeks, 9 weeks, 10 weeks, 11 weeks, or 12 weeks. In some embodiments, the gestational age of the fetus is 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days 42 days, 49 days, 56 days, 63 days, 70 days, 77 days, or 84 days, or a range defined by any of the preceding values, for example 35-53 days, or 42-49 days.

Assay Performance

The methods, compositions, and kits of the disclosure may be used in assays to determine fetal sex in a pregnant subject. Fetal sex assay performance can be assessed by determining the assay's sensitivity, specificity, area under the ROC curve (AUC), accuracy, positive predictive value (PPV), and negative predictive value (NPV). Disclosed herein are assays for determining fetal sex in a pregnant subject.

The performance of the assay may be based on sensitivity. The sensitivity of an assay of the disclosure may be at least about 40%, 45%, 50%, 55%, 60%, 65%, 70%, 75%, 80%, 85%, 90%, 91%, 92%, 93%, 94% 95%, 96%, 97%, 98%, 99%, or 100%. The performance of the assay may be based on specificity. The specificity of an assay of the disclosure may be at least about 40%, 45%, 50%, 55%, 60%, 65%, 70%, 75%, 80%, 85%, 90%, 91%, 92%, 93%, 94% 95%, 96%, 97%, 98%, 99%, or 100%. The performance of the assay may be based on area under the ROC curve (AUC). The AUC of an assay of the disclosure may be at least about 0.5, 0.55, 0.6, 0.65, 0.7, 0.75, 0.8, 0.85, 0.9, or 0.95. The performance of the assay may be based on accuracy. The accuracy of an assay of the present disclosure may be at least about 40%, 45%, 50%, 55%, 60%, 65%, 70%, 75%, 80%, 85%, 90%, 91%, 92%, 93%, 94% 95%, 96%, 97%, 98%, 99%, or 100%.

The performance of the methods, compositions, and kits of the disclosure have been determined in multiple populations. In some embodiments, the performance of the methods, compositions, and kits of the disclosure have been determined in a population of at least 10, 20, 30, 40, 50, 60, 70, 80, 90, 100, 150, 200, 300, 400, 500, and/or 1,000 or more pregnant subjects. In certain aspects the accuracy of an assay of the disclosure is determined in a population of at least 10, 20, 30, 40, 50, 60, 70, 80, 90, 100, 150, 200, 300, 400, 500, and/or 1,000 or more pregnant subjects. In certain aspects the sensitivity of an assay of the disclosure is determined in a population of at least 10, 20, 30, 40, 50, 60, 70, 80, 90, 100, 150, 200, 300, 400, 500, and/or 1,000 or more pregnant subjects. In certain aspects the specificity of an assay of the disclosure is determined in a population of at least 10, 20, 30, 40, 50, 60, 70, 80, 90, 100, 150, 200, 300, 400, 500, and/or 1,000 or more pregnant subjects.

Y-Chromosome Detection

The disclosure provides methods, compositions, and kits for detecting Y-chromosome nucleic acids in a biological sample obtained from a pregnant subject. In some embodiments, the Y-chromosome nucleic acids are cell-free fetal nucleic acids (e.g., cffDNA). In some embodiments, the Y-chromosome nucleic acids are genomic fetal nucleic acids from a fetal cell (e.g., gfDNA).

The disclosure also provides methods for isolating and concentrating fetal nucleic acids in biological samples from pregnant subjects. In some embodiments, the methods further comprise isolating fetal nucleic acids with a silica column or magnetic beads. In other embodiments, the methods further comprise concentrating the fetal nucleic acids in the biological sample using heat. In yet other embodiments, the methods further comprise isolating fetal nucleic acids by incubating the sample with an enzyme (e.g., proteinase K).

The disclosure provides methods, compositions, and kits for detecting Y-chromosome nucleic acids in a biological sample from a pregnant subject. In some embodiments, the detecting comprises performing microarray analysis, polymerase chain reaction (PCR), or sequencing. In some embodiments, the PCR is quantitative PCR (qPCR) or digital PCR. In other embodiments the qPCR is a TaqMan assay. In other embodiments, the PCR is a nested PCR, a duplex PCR, or a multiplex PCR. In other embodiments, the reaction volume of the PCR is 2 ul, 3 ul, 4 ul, 5 ul, 10 ul, 15 ul, 20 ul, 25 ul, or 50 ul. In yet other embodiments, the mastermix used in the PCR contains Uracil N Glycosylase (UNG).

The disclosure provides compositions for detecting Y-chromosome nucleic acids in a biological sample. In some embodiments, the compositions are primers and/or probes that are capable of amplifying and detecting at least one target sequence on the Y-chromosome. The probe set may comprise one or more polynucleotide probes. Individual polynucleotide probes comprise a nucleotide sequence derived from the nucleotide sequence of the target sequences or complementary sequences thereof. The nucleotide sequence of the polynucleotide probe is designed such that it corresponds to, or is complementary to the target sequences. The polynucleotide probe can specifically hybridize under either stringent or lowered stringency hybridization conditions to a region of the target sequences. The selection of the polynucleotide probe sequences and determination of their uniqueness may be carried out in silico using techniques known in the art, for example, based on a BLASTN search of the polynucleotide sequence in question against gene sequence databases, such as the Human Genome Sequence, UniGene, dbEST or the non-redundant database at NCBI. In one embodiment of the disclosure, the polynucleotide probe is complementary to a region of a target mRNA derived from a target sequence in the probe set. Computer programs can also be employed to select probe sequences that may not cross hybridize or may not hybridize non-specifically.

The polynucleotide target sequences of the disclosure may range in length from about 15 nucleotides to the full length of the target sequence on the Y-chromosome. In one embodiment of the disclosure, the polynucleotide target sequences are at least about 15 nucleotides in length. In another embodiment, the polynucleotide target sequences are at least about 20 nucleotides in length. In a further embodiment, the polynucleotide target sequences are at least about 25 nucleotides in length. In another embodiment, polynucleotide target sequences are between about 15 nucleotides and about 500 nucleotides in length. In other embodiments, the polynucleotide target sequences are between about 15 nucleotides and about 450 nucleotides, about 15 nucleotides and about 400 nucleotides, about 15 nucleotides and about 350 nucleotides, about 15 nucleotides and about 300 nucleotides, about 15 nucleotides and about 250 nucleotides, about 15 nucleotides and about 200 nucleotides in length. In some embodiments, the probes are at least 15 nucleotides in length. In some embodiments, the target sequences are at least 15 nucleotides in length. In some embodiments, the target sequences are at least 20 nucleotides, at least 25 nucleotides, at least 50 nucleotides, at least 75 nucleotides, at least 100 nucleotides, at least 125 nucleotides, at least 150 nucleotides, at least 200 nucleotides, at least 225 nucleotides, at least 250 nucleotides, at least 275 nucleotides, at least 300 nucleotides, at least 325 nucleotides, at least 350 nucleotides, at least 375 nucleotides in length.

The present disclosure further provides primers and primer pairs capable of amplifying target sequences on the Y-chromosome. The nucleotide sequences of the primer set may be provided in computer-readable media for in silico applications and as a basis for the design of appropriate primers for amplification of one or more target sequences of the primer set.

Primers based on the nucleotide sequences of target sequences can be designed for use in amplification of the target sequences. For use in amplification reactions such as PCR, a pair of primers can be used. The pairs of primers are usually chosen so as to generate an amplification product of at least about 25 nucleotides, at least about 50 nucleotides, at least about 100 nucleotides, at least about 150 nucleotides, at least about 200 nucleotides, at least about 250 nucleotides, at least about 300 nucleotides. These primers may be used in standard quantitative or qualitative PCR-based assays to detect the presence of fetal Y-chromosome nucleic acids in the biological sample. Alternatively, these primers may be used in combination with probes, such as TaqMan probes or molecular beacons in amplifications using real-time PCR.

In one embodiment, the primers or primer pairs, when used in an amplification reaction, specifically amplify at least a portion of a nucleic acid sequence of a target selected from the Y-chromosome. In some embodiments, the target sequences are present on the Y-chromosome in multiple locations. In certain embodiments, the target sequences are present in 2, 3, 4, 5, 6, 7, 8, 9, 10, about 15, about 20, about 25, about 50, about 75, about 100, about 150, about 200, about 300, about 400, about 500, about 750, about 1,000 locations on the Y-chromosome. The sensitivity of assays of the disclosure can be increased by detecting and/or amplifying target sequences that are present on the Y-chromosome in multiple locations. Multiple primer pairs can be used in the methods of the disclosure. For example, a duplex or multiplex qPCR assay may be used to increase the detection limit of an assay of the disclosure. A label can be attached to or incorporated into a probe or primer polynucleotide to allow detection and/or quantitation of a target polynucleotide representing the target sequence of interest.

The analysis of a plurality of target sequences on the Y-chromosome may be carried out separately or simultaneously with one test sample. In some embodiments, the target on the Y-chromosome is SRY, DYS, and/or DAZ. An assay consisting of a combination of the target sequences referenced in the instant disclosure may be constructed. Such a panel may be constructed using 1, 2, 3, 4, 5, 6, 7, 8, 9, 10, 15, 20, or more or target sequences. The analysis of a single target sequence or subsets of target sequences comprising a larger panel of Y-chromosome targets could be carried out with the methods described within the instant disclosure to optimize assay sensitivity or specificity in various settings. The ratio of a target sequence on the Y-chromosome and a control sequence from an autosomal chromosome may be used in an algorithm of the disclosure for determining fetal sex.

The methods, compositions, and kits of the disclosure can be used to detect very small amounts of Y-chromosome DNA in a biological sample from a pregnant subject. In some embodiments, the methods of the disclosure can detect about 1 to 0.1 genomic equivalent of cffDNA in a sample, about 0.9 genomic equivalent of cffDNA in a sample, about 0.8 genomic equivalent of cffDNA in a sample, about 0.7 genomic equivalent of cffDNA in a sample, about 0.6 genomic equivalent of cffDNA in a sample, about 0.5 genomic equivalent of cffDNA in a sample, about 0.4 genomic equivalent of cffDNA in a sample, about 0.3 genomic equivalent of cffDNA in a sample, about 0.2 genomic equivalent of cffDNA in a sample, about 0.1 genomic equivalent of cffDNA in a sample. In other embodiments, the methods of the disclosure can detect a single copy of Y-chromosome DNA.

In some embodiments, the detecting comprises performing microarray analysis, polymerase chain reaction (PCR), or sequencing. In some embodiments, the PCR is quantitative PCR (qPCR) or digital PCR. In other embodiments, the qPCR is a TaqMan assay. In other embodiments, the PCR is a nested PCR, a duplex PCR, or a multiplex PCR. In other embodiments, the reaction volume of the PCR is 2 ul, 3 ul, 4 ul, 5 ul, 10 ul, 15 ul, 20 ul, 25 ul, or 50 ul. In yet other embodiments, the mastermix used in the PCR contains Uracil N Glycosylase (UNG). In other embodiments, the methods further comprise interpreting data generated when detecting the Y-chromosome DNA. In some embodiments, the interpreting is performed using a machine learning algorithm, a cycle-threshold (CT) algorithm, or artificial intelligence.

Kits

Another aspect of the disclosure encompasses kits for collecting biological samples from pregnant subjects or for detecting Y-chromosome nucleic acids in a biological sample from a pregnant subject. A variety of kits having different components are contemplated by the disclosure. Generally speaking, the kit will include the means for detecting Y-chromosome in a biological sample from a pregnant subject. In another embodiment, the kit will include means for collecting a biological sample and instructions for use of the kit contents. In certain embodiments, the kit comprises a means for enriching or isolating fetal nucleic acids in a biological sample. In further aspects, the means for enriching or isolating fetal nucleic acids comprises reagents necessary to enrich or isolate fetal nucleic acids from a biological sample.

The kits of the disclosure may include instructions for decontaminating the site on the pregnant subject where the sample will be collected. In certain embodiments, the decontamination is performed by applying bleach to the site of collection, by applying an alcohol wipe to the site of collection, by treating the site of collection with ultra-violet light, by applying chlorhexidine gluconate, hydrogen peroxide, and/or iodine to the site of collection, by applying a brush (e.g., a nail brush) to the site of the collection.

The present disclosure further provides kits for obtaining a biological sample from a pregnant subject. The kits may comprise a blood collection tube, a lancet or a device useful for obtaining venous or capillary blood from the subject, a tourniquet, a bandage, an alcohol swab, a nail or skin brush, and instructions for using the kits. In some embodiments, the kits further comprise a decontaminating agent. In certain embodiments, the decontaminating agent is bleach, an alcohol wipe, chlorhexidine gluconate, hydrogen peroxide, and/or iodine. In other embodiments, the device for obtaining venous or capillary blood is a lancet (e.g., BD Microtainer contact-activated lancet), a syringe, and/or a push-button blood collection device (e.g., a TAP device). In some embodiments, the biological sample is collected into a tube, onto a card, and/or a swab.

Methods and kits of the disclosure can include instructions that provide a minimum gestational age or gestational age range for sample collection. In some embodiments, the minimum gestational age is 2 weeks, 3 weeks, 4 weeks, 5 weeks, 6 weeks, 7 weeks, 8 weeks, 9 weeks, 10 weeks, 11 weeks, or 12 weeks. In some embodiments, the gestational age is 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days 42 days, 49 days, 56 days, 63 days, 70 days, 77 days, or 84 days.

These and other embodiments of the present disclosure will readily occur to those of ordinary skill in the art in view of the disclosure herein.

EXAMPLES

The disclosure will be further understood by reference to the following examples, which are intended to be purely exemplary of the disclosure. These examples are provided solely to illustrate the claimed disclosure. The present disclosure is not limited in scope by the exemplified embodiments, which are intended as illustrations of single aspects of the disclosure only. Any methods that are functionally equivalent are within the scope of the disclosure. Various modifications of the disclosure in addition to those described herein will become apparent to those skilled in the art from the foregoing description. Such modifications are intended to fall within the scope of the appended claims.

Example 1: Determination of Fetal Sex at 28 Days Gestation

Whole blood samples are collected from pregnant woman of gestational age 28 days. The samples are used to validate a fetal sex test described herein using circulating cell free fetal DNA (ccffDNA) in maternal plasma.

One hundred and fifty participants from a clinic are enrolled in this study. Fetal gestational age of participants will be 4 weeks at the time of sample collection. Fetal sex test results are confirmed through subsequent sonographic evaluation after participants reach at least 14 weeks gestation.

At the time of sample collection, 3-4 mL of maternal blood is drawn from all participants by standard venipuncture. Additionally, 500 ul of maternal capillary blood is collected via fingerstick using a standard lancet. Approximately 500 μL of the collected sample is centrifuged at 1,600 g for 15 minutes to separate plasma from whole blood. Next, 100 μL of the separated plasma is incubated with Proteinase K to help degrade any proteins that may have been bound to the DNA. Following proteinase K treatment, cfDNA is isolated from the plasma samples using a MagMAX Cell-Free DNA Isolation Kit (ThermoFisher) according to the manufacturer's instructions.

Real-time quantitative polymerase chain reaction (RT-qPCR) is utilized to detect male cell-free fetal DNA as follows. Isolated cell-free DNA (5 ul) is dispensed into 96-well plates and reacted with a custom master mix for a final PCR reaction volume of 25 ul per well. Male cell-free DNA is detected using a multi-copy target sequence on the Y-Chromosome. An autosomal control gene is detected to confirm that a sufficient amount of total cfDNA (maternal and fetal) was isolated from the sample. The cycling conditions for the PCR are set at 10 min at 95° C. to allow for the initial denaturation of DNA and polymerase activation, followed by 45 cycles of one minute at 60° C. and 15 seconds at 95° C.

An algorithm that incorporates the cycle threshold (CT) value of the Y-target sequence and autosomal control gene PCR reactions is utilized to determine fetal sex. The results of the fetal sex assay are confirmed through sonographic evaluation at the conclusion of the study.

Male Y-chromosome DNA is detected in all samples from women carrying a male fetus. The fetal sex test correct identifies fetal sex in all 150 pregnancies. In this study, the fetal sex test's accuracy, sensitivity, and specificity are 100%, 100%, and 100% for fetal sex identification, respectively.

These results show that a fetal sex test of the present disclosure can accurately determine fetal sex as early as 4 weeks into pregnancy (i.e., 4 weeks gestational age) with up to 100% accuracy. These results also show that the methods and compositions of the present disclosure are useful for determining fetal sex in early pregnancy (as early as 4 weeks gestational age). The results demonstrate that the disclosure provides methods, assays, kits, and compositions for detecting fetal nucleic acids and determining fetal sex in early pregnancy (e.g., 4 weeks gestation).

Example 2: Determination of Fetal Sex at 8 Weeks Gestation

The purpose of this study was to evaluate the clinical performance of an assay of the disclosure for noninvasive prenatal testing (NIPT) to determine fetal sex at 8 weeks gestation. One hundred and eight participants were enlisted for this study. Fetal gestational age of participants ranged from 7.00-10.57 weeks at the time of sample collection. Fetal sex test results were confirmed through subsequent sonographic evaluation after participants had reached at least 14 weeks gestation.

At the time of sample collection, 3-4 mL of maternal blood was drawn from all participants by standard venipuncture. Blood samples were sent to a clinical lab where 600 μL of the collected sample was then centrifuged at 1,600 g for 15 minutes to separate plasma from whole blood. Next, 100 μL of the separated plasma was incubated with Proteinase K. Following proteinase K treatment, cfDNA was isolated from the plasma samples using the MagMAX Cell-Free DNA Isolation Kit (ThermoFisher) according to the manufacturer's instructions. Real-time quantitative polymerase chain reaction was utilized to detect male cell-free fetal DNA as follows. Isolated cell-free DNA (5 ul) was dispensed into 96-well plates and reacted with a custom master mix for a final PCR reaction volume of 25 ul per well. Male cell-free DNA was detected using a multi-copy target sequence on the Y-Chromosome. An autosomal control gene was detected to confirm that a sufficient amount of total cfDNA (maternal and fetal) was isolated from the sample. The cycling conditions for the PCR were set at 10 min at 95° C. to allow for the initial denaturation of DNA and polymerase activation, followed by 45 cycles of one minute at 60° C. and 15 seconds at 95° C. An algorithm that incorporated the cycle threshold (CT) value of the Y-target sequence and autosomal control gene PCR reactions was utilized to determine fetal sex. The results of the fetal sex assay were confirmed through sonographic evaluation at the conclusion of the study.

Fetal sex was determined for all 108 participants. In this study, there were 51 male bearing pregnancies and 57 female bearing pregnancies. The fetal sex test correctly identified all 51 male bearing pregnancies, demonstrating 100% sensitivity for Y-chromosome DNA detection. There were 0 false negatives resulting in a positive predictive value of 100%. The fetal sex test correctly identified 56 of 57 female bearing pregnancies. There was one false positive resulting in a negative predictive value of 98%. Four of the 108 samples initially yielded an inconclusive result. A second sample was collected from the four participants and a result was obtained on the second round of testing.

The average CT value for the Y-target sequence for plasma from male bearing pregnancies was 29.89 ranging from 28.09-32.03. Total cfDNA for both male bearing pregnancies and female bearing pregnancies were comparable. The average CT value for total DNA in male bearing pregnancies was 32.81, with a range of 31.13-34.63. The average CT value for the female bearing pregnancies was 32.93, with a range of 29.97-35.15.

In this study, the fetal sex test was shown to be 99.1% accurate for fetal sex determination at 8 weeks gestation and 100% sensitive for male fetal cell-free DNA. These results showed that the methods and compositions of the disclosure are useful for determining fetal sex as early as 8 weeks gestation using a microvolume amount of maternal plasma.

Example 3: Determination of Fetal Sex at Six Weeks Gestation

The purpose of this study was to evaluate the clinical performance of an assay of the disclosure for noninvasive prenatal testing (NIPT) to determine fetal sex at six weeks gestation in assisted reproductive technology achieved (ART) pregnancies. Eighteen participants undergoing ART pregnancy were enrolled in this study. A venipuncture blood draw was collected from each participant at approximately 42 days gestation. Samples were processed and tested approximately 24-48 hours after collection. Fetal sex was known at the time of embryo implantation from preimplantation genetic testing (PGT). The accuracy of the test was assessed by comparing the qPCR test results from maternal blood samples obtained at day 42 of gestation to the fetal sex results obtained from PGT.

At the time of sample collection, 3 mL of maternal blood was drawn from all participants by standard venipuncture. Blood samples were mailed to a clinical lab and the blood sample was centrifuged at 1,600 g for 15 minutes to separate plasma from whole blood. Next, 100 μL of the separated plasma was incubated with Proteinase K. Following proteinase K treatment, cfDNA was isolated from the plasma samples using a MagMAX Cell-Free DNA Isolation Kit (ThermoFisher) according to the manufacturer's instructions. Real-time quantitative polymerase chain reaction was utilized to detect male cell-free fetal DNA as follows. Isolated cell-free DNA (5 ul) was dispensed into 96-well plates and reacted with a custom master mix for a final qPCR reaction volume of 25 ul per well. Male cell-free DNA was detected using a multi-copy target sequence on the Y-Chromosome. An autosomal control gene was detected to confirm that a sufficient amount of total cfDNA (maternal and fetal) was isolated from the sample. The cycling conditions for the qPCR were set at 10 min at 95° C. to allow for the initial denaturation of DNA and polymerase activation, followed by 45 cycles of one minute at 60° C. and 15 seconds at 95° C. An algorithm that incorporated the cycle threshold (CT) value of the Y-target sequence and autosomal control gene qPCR reactions was utilized to determine fetal sex. The accuracy of the test was assessed by comparing the qPCR test results from maternal blood samples obtained at day 42 of gestation to the fetal sex results obtained from PGT.

Fetal sex was determined for all 18 participants. In this study, there were 6 male bearing pregnancies and 12 female bearing pregnancies. The fetal sex test correctly identified all 6 male bearing pregnancies, demonstrating 100% sensitivity for Y-chromosome DNA detection. There were no false negatives resulting in a positive predictive value of 100%. The fetal sex test correctly identified 12 of 12 female bearing pregnancies. There were no false positives resulting in a negative predictive value of 100%.

The average CT value for the Y-target sequence for plasma from male bearing pregnancies was 30.55 ranging from 29.48-31.16. Total cfDNA for both male bearing pregnancies and female bearing pregnancies were comparable. The average CT value for total DNA in male bearing pregnancies was 31.75. The average CT value for the female bearing pregnancies was 31.82.

In this study, the fetal sex test was shown to be 100% accurate for fetal sex determination at 6 weeks gestation and 100% sensitive for male fetal cell-free DNA. These results were obtained using 100 ul of maternal plasma. These results showed that the methods and compositions of the disclosure are useful for determining fetal sex as early as 6 weeks gestation using a microvolume amount of maternal plasma. These results further showed that the methods of the disclosure are useful for providing greater than 99% accurate fetal sex test results from biological samples stored at ambient temperature for 24-48 hours before processing.

Example 4: Determination of Fetal Sex at 8 Weeks Gestation Using a TAP Blood Collection Device The purpose of this study was to evaluate the performance of a fetal sex assay at eight- and nine-weeks gestation in capillary whole blood samples collected with a TAP blood collection device. Twenty-six pregnant women were enrolled in this study. A capillary blood sample was collected from each participant at approximately 8 to 9 weeks gestation. Samples were processed and tested approximately 24-72 hours after collection. The accuracy of the test was assessed by comparing the qPCR test results from maternal blood samples to sonogram evaluations performed after 14 weeks gestation.

At the time of sample collection, 100 uL of maternal capillary blood was collected from the upper arm of all participants using a TAP blood collection device per the manufacturer's instructions (Seventh Sense Biosystems, MA). TAP devices containing the blood samples were mailed to a clinical lab and the blood sample was removed from the device with a pipette and subsequently centrifuged at 1,600 g for 15 minutes to separate plasma from whole blood. Next, 50 μL of the separated plasma was incubated with Proteinase K. Following proteinase K treatment, cfDNA was isolated from the plasma samples using a MagMAX Cell-Free DNA Isolation Kit (ThermoFisher) according to the manufacturer's instructions. Real-time quantitative polymerase chain reaction was utilized to detect male cell-free fetal DNA as follows. Isolated cell-free DNA (5 ul) was dispensed into 96-well plates and reacted with a custom master mix for a final qPCR reaction volume of 25 ul per well. Male cell-free DNA was detected using a multi-copy target sequence on the Y-Chromosome. An autosomal control gene was detected to confirm that a sufficient amount of total cfDNA (maternal and fetal) was isolated from the sample. The cycling conditions for the qPCR were set at 10 min at 95° C. to allow for the initial denaturation of DNA and polymerase activation, followed by 45 cycles of one minute at 60° C. and 15 seconds at 95° C. An algorithm that incorporated the cycle threshold (CT) value of the Y-target sequence and autosomal control gene qPCR reactions was utilized to determine fetal sex. The accuracy of the test was assessed by comparing the qPCR test results from maternal blood samples to sonogram evaluations performed after 14 weeks gestation.

Fetal sex was determined for all 26 participants. The fetal sex test correctly identified the sex of the fetus in all 26 pregnancies, demonstrating 100% sensitivity and 100% specificity for Y-chromosome DNA detection and 100% accuracy for fetal sex determination. There were no false positive or false negatives.

In this study, the fetal sex test was shown to be 100% accurate for fetal sex determination as early as 8 weeks gestation using 50 ul of plasma collected with a TAP blood collection device. These results showed that the methods and compositions of the disclosure are useful for determining fetal sex as early as 8 weeks gestation using a microvolume amount of maternal plasma with a TAP blood collection device. These results further showed that the methods of the disclosure are useful for providing greater than 99% accurate fetal sex test results from biological samples stored at ambient temperature for 24-72 hours before processing.

Various modifications of the disclosure, in addition to those shown and described herein, will become apparent to those skilled in the art from the foregoing description. Such modifications are intended to fall within the scope of the appended claims.

All references cited herein are hereby incorporated by reference herein in their entirety.

What is claimed is:

1. A method of improving the accuracy of fetal sex determination by reducing a level of contaminating DNA in a blood sample from a pregnant human subject, the method comprising:
    a.) obtaining a 100-750 µl capillary blood sample that was collected from the upper arm of the human subject into a tube using a push-button blood collection device, thereby reducing a level of contaminating DNA from a non-maternal and non-fetal source in the capillary blood sample as compared to a blood sample from the subject collected from a site on the finger or hand of the subject;
    b.) separating plasma from the capillary blood sample;
    c.) isolating cell-free nucleic acids from the plasma; and
    d.) performing PCR on the cell-free nucleic acid to detect the presence or absence of fetal Y-chromosome nucleic acids in the capillary blood sample, thereby determining the sex of the fetus.

2. The method of claim 1, wherein the push-button blood collection device is a sterilized blood collection device configured to use a combination of capillary action and vacuum extraction, the device comprising a layer of adhesive configured to seal the device to the skin and hold the device in place during use, and an array of microneedles configured to puncture through the skin when activated by the user pushing a button or plunger on the device.

3. The method of claim 1, wherein the probability that the capillary blood sample contains contaminating DNA from a non-maternal and a non-fetal source is reduced compared to a blood sample collected from a site on the finger or hand of the subject.

4. The method of claim 1, wherein the capillary blood sample is free of contaminating DNA from a non-maternal and a non-fetal source.

5. The method of claim 1, wherein the sex of the fetus is determined with at least 99.5% accuracy determined in a population of at least 50 pregnant human subjects.

6. The method of claim 1, wherein the false positive rate of the method is less than 1% determined in a population of at least 50 pregnant human subjects.

7. The method of claim 1, wherein the false positive rate of the method is 0% determined in a population of 26 pregnant human subjects.

8. The method of claim 1, wherein the probability of a false positive is reduced compared to the probability of a false positive for the same method performed on a blood sample collected from a site on the finger or hand of the subject.

9. The method of claim 1, wherein the gestational age of the fetus is 6 weeks to 12 weeks.

10. The method of claim 1, wherein the PCR is a real-time quantitative PCR.

11. The method of claim 1, wherein the capillary blood sample is contacted with a preservative present in the tube.

12. The method of claim 11, wherein the capillary blood sample is stored at ambient temperature for at least 12 hours before the separating the plasma from the capillary blood sample.

13. The method of claim 11, wherein the preservative comprises an anti-coagulant, a cell stabilizer, and a DNA preservative.

14. The method of claim 13, wherein the anti-coagulant is selected from ethylenediaminetetraacetic acid (EDTA), ethylene glycol-bis(β-aminoethyl ether)-N,N,N',N'-tetraacetic acid (EGTA), and heparin.

* * * * *